United States Patent [19]

Ijzerman et al.

[11] Patent Number: 5,527,667
[45] Date of Patent: Jun. 18, 1996

[54] WATER SAMPLE VIRAL CONTAMINATION DETECTION SYSTEM

[75] Inventors: M. Marian Ijzerman; Charles Hagedorn; Joseph O. Falkinham, all of Blacksburg, Va.

[73] Assignees: Virginia Polytechnic Institute and State University; Virginia Tech Intellectual Properties, Inc., both of Blacksburg; The Center for Innovative Technology, Herndon, all of Va.

[21] Appl. No.: 66,865

[22] Filed: May 25, 1993

[51] Int. Cl.$^6$ .................................................. C12Q 1/70
[52] U.S. Cl. .................... 435/5; 435/4; 435/18; 435/34; 435/38; 435/39
[58] Field of Search ................... 435/4.5, 18, 34, 435/38, 39; 436/20, 164; 422/82.05, 82.08

[56] References Cited

U.S. PATENT DOCUMENTS

| | | | |
|---|---|---|---|
| 3,002,892 | 10/1961 | Dooley | 435/5 |
| 3,416,998 | 12/1968 | Streitfeld | 435/5 |
| 3,870,601 | 3/1975 | Warren | 435/5 |
| 3,936,356 | 2/1976 | Janin | 435/38 |
| 3,957,589 | 5/1976 | Kronish etal. | 435/38 |
| 4,070,247 | 1/1978 | Burt | 435/38 |
| 4,308,348 | 12/1981 | Monget | 435/38 |
| 5,210,022 | 5/1993 | Roth et al. | 435/34 |

FOREIGN PATENT DOCUMENTS

| | | |
|---|---|---|
| 328106 | 8/1989 | European Pat. Off. |
| 332752 | 9/1989 | European Pat. Off. |

OTHER PUBLICATIONS

Sales Brochure of Access Medical Systems, Inc., Cat. #IS–001 Jan. 1988 for Colilert MPN.

Censi et al; "Fluorogenic Detection of Atypical Coliforms from Water Samples"; (ABS); Microbiologica; 13(2); 1990; pp. 121–130 (Abstract).

Wybroski et al; "Analysis of Inducers of *E. coli* Lac . . . "; Nucleic Acid Research; 19(17); 4647–4653; 1991.

Ijerman et al; "Improved Method for Coliphage Detection . . . "; J. Virol. Meth,; 40;31–36; 1992.

Warren et al; "Rapid Enumeration of Fecal Coliforms . . . "; Appl. Enviro. Microbiol., 35(1); Jan 1978; 136–141.

Munro et al; "Changes in *E. coli* Cells . . . "; Appl. Env. Microb.; 53(7); Jul. 1987; pp. 1476–1481.

Elliot et al; "The Catalytic Consequences of Experimental Evolution"; Biochem. J.; 282(pt1); 155–164. 1992.

Musso et al; "Substrate Specificity and Kinetic Studies on Thiogalactoside . . . "; Biochemistry; 12(3), 1973, pp. 553–557.

American Public Health Association, Standard Methods for the Examination of Water and Wastewater, Seventeenth Edition, pp. 9211–9212.

*Primary Examiner*—Jill Warden
*Assistant Examiner*—Jan M. Ludlow
*Attorney, Agent, or Firm*—Whitham, Curtis, Whitham & McGinn

[57] ABSTRACT

Viral contamination in water samples is detected using a medium which includes both a substrate for β-galactosidase and *E. coli* with elevated levels of intracellular β-galactosidase. The substrate is chosen to undergo a detectable change (e.g., colorimetric, fluorometric, photometric, etc.) upon cleavage by β-galactosidase. A water sample to be tested for viral contamination is added to the medium. If coliphages are present in the water sample, they will infect, multiply within, and subsequently lyse the *E. coli* host. Lysis of the *E. coli* will allow the release of the intracellular β-galactosidase into the media, whereupon the enzyme will cleave the substrate for a detectable reaction. In one particular application, a colorimetric reagent that serves as a substrate for β-galactosidase is dissolved or dispersed within an agar medium, and in another particular application, a colorimetric reagent that serves as a substrate for β-galactosidase is dissolved or dispersed within a liquid medium. Color changes which result from lytic cell infection of the *E. coli* hosts are easily monitored by researchers or laboratory technicians. The presence of coliphages in a water sample is indicative of the presence of harmful human and animal enteric viruses in the water.

9 Claims, No Drawings

WATER SAMPLE VIRAL CONTAMINATION DETECTION SYSTEM

BACKGROUND OF THE INVENTION

1. Field of the Invention

This invention is generally related to the detection of viral contaminants in ground and surface waters and, more particularly, to qualitative and quantitative testing systems for quick and accurate detection of viral contamination.

2. Description of the Prior Art

In 1914, the United States Public Health Service adopted the coliform group of bacteria (total and fecal) as the accepted indicator of fecal pollution of drinking water. Even though many bacteria included in the coliform group are not of fecal origin, research on microbial indicators supports the conclusion that the coliform standard is a satisfactory indicator of bacterial fecal contamination. However, there are serious concerns that the coliform group may not be a reliable indicator of viral fecal contamination. Many enteric viruses are more resistant than *Escherichia coli* to a variety of adverse environmental conditions and waste treatment processes, including chlorination, because of their acellular nature and highly resistant protein coat.

Viruses found in domestic sewage can pose a greater health problem for humans than bacteria because the dose required to cause sickness is much less than with bacteria. Documented waterborne outbreaks of viral disease have largely been limited to the agent of infectious hepatitis because of its characteristic symptomology. Other waterborne virus disease outbreaks have not been as easily recognized, and well documented outbreaks attributable to many specific enteric viruses are lacking.

There is presently no routine drinking water examination procedure for enteric viruses because of the cumbersome isolation techniques that include mammalian cell cultures, high costs of materials, and the need for skilled laboratory personnel experienced in enteric virus isolation and enumeration techniques.

There is a growing consensus among scientists that coliphages, which are viruses that infect *E. coli*, can be used as indicator organisms for the presence of human pathogenic viruses, much in the same way as coliforms are used to indicate the possible presence of bacterial pathogens. Coliphages are an extensive and diverse group of viruses that include medium and large DNA bacteriophages, small genome DNA viruses, and single and double stranded DNA and RNA viruses. The most frequently reported or routinely isolated are the medium and large DNA coliphages such as T-phages, phage lambda, P2–4 phages, and the lipid containing phages. Many of the DNA coliphages are of roughly the same size and molecular weight as the more common enteric viruses and can be used as models for enteric virus survival. Reports suggest that coliphages and enteric viruses are removed at comparable rates during treatment processes, that certain coliphages are at least as resistant to environmental stresses and to chlorination as enteric viruses, and that coliphages exhibit a seasonal variation similar to that of enteric viruses. Currently, coliphage detection as an indicator of the sanitary quality of water has been proposed by the American Public Health Association and is under serious consideration (see, *Standard Methods for the Examination of Water and Wastewater*, 1989, 17th ed., L. S. Clesceri et al. (eds.), Sections 9–36 & 9–37, Amer. Public Health Assoc., Wash. D.C.).

The method proposed by the American Public Health Association (APHA) for the detection and enumeration of coliphages from ground and surface water is a single-agar-layer plaque technique which is analogous to colony counting in bacteria. It is recommended that *E. coli* C (ATCC 13706) be used as the host (because it is a restriction-less strain which prevents infecting phage DNA degradation), and that 2,3,5-triphenyl tetrazolium chloride (TPTZ) be added to the agar as an oxidation-reduction agent to provide a contrast to detect cleared zones (plaques). In the APHA method, as non-infected *E. coli* cells grow, the TPTZ is reduced and lends a pale pink color to the agar while plaques (infected and killed *E. coli*) remain colorless. Plaques are then counted to provide enumeration of the number of coliphages in the original water sample.

SUMMARY OF THE INVENTION

It is an object of this invention to provide qualitative and quantitative viral contamination detection systems for water sample analysis through the use of a coliphage indicator.

According to the invention, an *E. coli* culture is grown in the presence of an inducer compound that promotes the production of the enzyme β-galactosidase. The *E. coli* culture can be grown in either liquid or agar media which contains a colorimetric reagent (chromogenic agent) which can be acted on by β-galactosidase to produce a detectable color change. Water samples to be tested for viral contamination are added to the *E. coli* culture. If coliphages are present in the water sample, they will infect the *E. coli*, form multiple copies, and subsequently lyse the *E. coli* cells. Lysis of the *E. coli* cells allows the release of β-galactosidase into the liquid or agar media which results in a color change in the colorimetric reagent via the enzymatic action of β-galactosidase on the colorimetric reagent. The presence of coliphages in water samples is indicative of the presence of other viruses that are harmful to humans and other animals. If coliphages are not detected in a water sample, no color change will be observed, thus indicating the water sample is likely to be free of viral contamination.

The liquid media detection system provides a quick, qualitative indication of coliphage contamination in a water sample. The agar media detection system can be used to quantify the degree of coliphage contamination in a water sample. In the agar media detection system, coliphage numbers are estimated by counting plaques, which are lysed *E. coli* cells, that appear on the surface of the agar medium. β-galactosidase, which is released from the cell due to a lytic cell infection, reacts with a chromogenic agent, thereby forming a (dark blue) colored circle within each plaque. By convention, one plaque is equivalent to one coliphage particle. The number of plaques which are counted can be extrapolated to provide an accurate measure of the amount of coliphages in the body of water from which the sample was drawn.

The viral contamination detection systems are highly sensitive because infection by only a single coliphage present in a water sample allows both multiple copies of the coliphage to be formed in the *E. coli* host and the subsequent release of many copies of a host enzyme that will provide enhanced formation of a detectable colored product (chromogen). This amplification of the effect of infection by a single coliphage in terms of the ability to observe a color change allows very low levels of viral contamination to be detected.

DETAILED DESCRIPTION OF THE PREFERRED EMBODIMENTS OF THE INVENTION

Agar-based and liquid-based systems and methods for assessing viral contamination of water have been developed. The systems and methods discussed below utilize phage-induced lysis and release of induced β-galactosidase from *E. coli* strain C; however, it should be understood that all strains of *E. coli*, both donor and recipient, and mutants thereof which include the lacZ gene, can be employed within the practice of this invention. β-Galactosidase is encoded by the lacZ gene of the lac operon, and is an essential enzyme in the metabolism of lactose. Two known synthetic inducers of β-galactosidase are isopropyl-β-D-thiogalactoside (IPTG) and methyl-β-D-thiogalactoside (TMG). IPTG is the most powerful inducer of β-galactosidase. In the absence of an inducer, β-galactosidase levels have been detected to be fewer than ten molecules per cell; however, while in the presence of IPTG, β-galactosidase levels are increased by over a thousand-fold. TMG is an inducer which can be made radioactive. Lactose and its analogs can serve as both an inducer of β-galactosidase production and a substrate for β-galactosidase.

In both the agar-based and liquid-based coliphage detection systems and methods, a water sample is added to an *E. coli* cell culture that has been induced to make many copies of the enzyme β-galactosidase. If coliphages are present in the water sample, the coliphages will infect the *E. coli*, multiply within the *E. coli* hosts, and subsequently lyse the *E. coli* cells, thereby causing the release of many copies of the β-galactosidase into the surrounding medium. To detect whether or not the enzyme has been released due to a lyric cell function, a colorimetric reagent (chromogenic agent) which serves as a substrate for β-galactosidase is added to the medium. Colorimetric reagents which can be employed as substrates for β-galactosidase include O-nitrophenyl-β-D-thiogalactoside (ONPG), 5-bromo- 4-chloro-3-indoyl-β, D-galactoside (X-gal), and chlorophenol red β, D-galactopyranoside (CPRG). If the β-galactosidase is present in the medium due to the lytic cell function of coliphages in the water sample, it will cleave the colorimetric reagent and a detectable colored reaction will occur. If no coliphages are present in the water sample, β-galactosidase will not be released into the medium and a color change will not occur.

In the agar-based system and method, the preferred colorimetric reagent was the non-inducer X-gal, which provides a deep blue 5-bromo-4-chloro-indigo when it is cleaved by β-galactosidase. In the liquid-based system and method, the preferred colorimetric reagent was the non-inducer CPRG, which is a water soluble substrate for β-galactosidase which is 10-times more sensitive than ONPG, and which provides a distinct chlorophenol red color when it is cleaved by β-galactosidase.

Other lac operon based chromogenic substrates may also be used within the practice of this invention.

EXAMPLE 1—AGAR ASSAY

A comparative study was performed to evaluate the inventive procedure against the method described in the 18th edition of *Standard Methods for the Examination of Water and Wastewater* (American Public Health Association, Wash. D.C., 1992) which is herein incorporated by reference. As explained above, the APHA method recommends that *E. coli* strain C (ATCC 13706) be used as the host since it is a restriction-less strain which prevents infecting phage DNA degradation, and that TPTZ be added to the agar to aid in counting plaques. As non-infected *E. coli* cells grow, the TPTZ is reduced to lend a pale pink color to the agar while plaques remain colorless. The APHA procedure was performed as suggested, and was only altered in the following way: the assay volume was tripled for ease of handling and divided between two 100×15 mm petri plates and the average plaque count recorded. The suggested APHA procedure will hereinafter be referred to has the TPTZ method.

The agar-based system and method of the present invention, which will hereinafter be referred to as the IPTG/X-gal method, involved the use of *E. coli* strain C (ATCC 13706) inoculated from a stock Luria-Bertani (LB) agar slant into 10 ml sterile LB broth plus 10% glycerol volume/volume (v/v), shaken at 240 oscillations per minute (osc/min), and incubated at 37° C. overnight. One-half ml of the culture was transferred to 25 ml sterile LB broth plus 10% glycerol (v/v) incubated at 37° C. and shaken at 240 osc/min until an optical density (O.D.) of 0.5 at 520 nm was obtained. This procedure assures a cell density of approximately $1 \times 10^9$ *E. coli* strain C colony forming units per milliliter (cfu/ml). The culture was maintained at −20° C. in a non-frost freezer no longer than 30 days to reduce the loss of host culture viability.

To conduct the IPTG/X-gal assay, the frozen culture of *E. coli* C was thawed in a 44° C. water bath. One ml of host was added to 18 ml of modified LB agar at 50° C. (to the ingredients of LB broth add ammonium nitrate ($NH_4NO_3$) at 1.6 g/L; strontium nitrate ($Sr(NO_3)_2$) at 0.21 g/L; and agar at 15 g/L). A water sample containing the coliphage (ATCC 13706-B2) was added along with 66 µl IPTG (200 mg/L) and 360 µl X-gal (10 mg/L dissolved in dimethylformamide (DMF)). Bacteriophage ATCC-B2 is "female-specific" or "recipient-specific" which means that it only infects and forms plaques on non-donor, $F^-$ non-F-plasmid-carrying strains. Donor-specific (i.e., infect only F-plasmid or other plasmid carrying strains) and non-specific (i.e., donor/recipient status-independent) coliphages, as well as different *E. coli* host strains and mutants thereof, could also be employed within the practice of this invention. The solution was swirled and evenly distributed into two 100×15 mm petri dishes and, after the agar hardened, the plates were inverted and incubated at 35° C. Pale blue plaques begin to appear after four hours and the color intensifies as each plaque develops after seven to eight hours. The blue color will further intensify if the plates are stored for a few hours at 4° C. The average plaque count was recorded.

Proof that the blue cleared zones were actually coliphage plaques was obtained by aseptically removing the cleared zones from the agar and using these as samples to perform a single-agar-layer plaque assay. Results demonstrated that each blue cleared zone contained thousands of discrete lyric particles consistent with the presence of phage particles. Final confirmation was obtained using a Zeiss 10CA transmission electron microscope to observe thin sections of the blue cleared zones removed from the agar plates (120 to $150 \times 10^3$ x). The electron micrographs demonstrated visible phage particles within the material prepared from the blue cleared zones.

Table 1 shows that the IPTG/X-gal method of this invention consistently detected twice as many plaques as compared to the TPTZ method. The mean separation between treatments was determined by Duncan's multiple range test when the overall F-test was significant at $p < 0.01$.

TABLE 1

Mean coliphage counts (10⁷) of three separate experiments[a] comparing the IPTG/X-gal method with the TPTZ method proposed by APHA

| | Mean Coliphage Count[b] (Plaque forming units per ml) | |
|---|---|---|
| Experiment | TPTZ | IPTG/X-gal |
| 1 | 29.3B | 50.3A |
| 2 | 19.4B | 45.9A |
| 3 | 20.6B | 43.7A |

[a]Each experiment consisted of six replications for a total of eighteen tests per method.
[b]Means in each experiment followed by the same letter are not significantly different using Duncan's multiple range test ($p < 0.01$).

Higher counts for the IPTG/X-gal method might be partially explained by the ease of detection of the IPTG/X-gal plaques. Specifically, a dark blue circle formed within the plaque creating a distinguishable mark which aided in counting. The blue circle is permanent and allows plaque detection even if overgrowth of the plaques by non-infected bacteria should occur. This is an important advantage of the new IPTG/X-gal method over the TPTZ method, since the TPTZ method produces a clear plaque surrounded by a pale pink background that is difficult to count. If overgrowth by non-infected bacteria of the TPTZ plates should occur, accurate plaque counts cannot be obtained. Furthermore, laboratory tests showed that when the TPTZ method proposed by the APHA was followed using modified LB agar instead of the recommended medium, modified TSB agar, high plaque counts were obtained.

This study indicates that approximately 50% of the coliphages in the prepared samples would have escaped detection had the proposed APHA coliphage detection procedure been employed. The results suggest that a superior quantitative measure of coliphage contamination in water samples can be obtained using the IPTG/X-gal method.

EXAMPLE 2—LIQUID ASSAY

The liquid, colorimetric coliphage detection system and method was developed using *E. coli* strain C (ATCC-13706), an F- (recipient) that lacks restriction and modification systems to prevent infecting phage DNA degradation and which is sensitive to a broad spectrum of sewage phages. The sewage coliphage (ATCC-13706-B2) was used to determine the sensitivity of the assay; however, other coliphages (e.g., non-donor spcific, donor specific, and recipient-specific) could be used within the practice of this invention.

*E. coli* strain C was grown (24 h at 37° C.) and stored no longer than 30 days at 4° C. on LB agar. A single colony was aseptically transferred into 10 ml LB broth supplemented with 5 mmol $CaCl_2 \cdot 2H_2O$ after autoclaving and 1.25 mmol $MgSO_4 \cdot 7H_2O$ prior to autoclaving. The culture was incubated at 37° C. and 200 rpm for one hour. After one hour, the culture was aseptically inoculated with 25 µl of IPTG and incubated at 37° C. and 200 rpm for an additional 30 min. At the end of 30 min., a concentrated water sample no greater than 1.25 ml was added to the culture. The culture was swirled and maintained at room temperature without shaking for 10–15 min. and then returned to the 37° C. shaker for an additional 105 min at 200 rpm.

The culture was added to a sterile 50 ml centrifuge tube and centrifuged at 6° C., 5000 rpm for 15 min. The supernatant was vacuum-filtered through a 0.2 µm low protein-binding filter into a sterile test tube. To 9 ml of Z buffer (see Miller et al., *Experiments in Molecular Genetics*, Cold Spring Harbour Laboratory, Cold Spring Harbor, N.Y., pp. 352–355), 1 ml of filtrate was added plus 100 µl of CPRG (5 mmol stock) and incubated at 37° C. for 30 min.

A positive coliphage test can be observed by the immediate development of red, in an initially yellow solution, that intensifies over a 15 min. period and further develops into a uniform purple-red color in 30 min. A negative coliphage test is visually observed by the uniform yellow throughout the test tube at the end of the 30 min incubation period. Sometimes, due to carry-over of small amounts of enzyme in the filtration apparatus, a slight red band of color will appear at the meniscus of the liquid in an otherwise yellow sample; however, such a sample should still be regarded as a negative result, since only a uniform red throughout the tube is positive.

The liquid, colorimetric presence-absence coliphage detection system and method can be completed and the results obtained in 4.5 h. The liquid detection system and method is simpler to perform than an agar medium detection system and method primarily due to the absence of agar and the difficulties associated with rapid hardening. The results obtained by the liquid detection system and method are easy to read and interpret, and do not require the use of a spectrophotometer.

Table 2 shows that, theoretically, the liquid, colorimetric presence-absence detection system and method can detect as few as 2 PFU/ml, which is an improvement over the APHA agar-based method that can only detect as few as 5 PFU/ml.

TABLE 2

The sensitivity of the liquid, colorimetric presence-absence coliphage detection assay using *E. coli* strain C as host

| Number (PFU) | Positive Samples (30 Min) | Total Number of Samples |
|---|---|---|
| 60 | 3 | 3 |
| 30 | 23 | 23 |
| 22 | 16 | 16 |
| 11 | 15 | 15 |
| 6[a] | 15 | 15 |
| 4[a] | 12(15)[b] | 15 |
| 2[a] | 8(11)[c] | 15 |
| 0 | 0 | 39 |

[a]Two ml of filtrate was added to 8 ml of Z buffer, while 1 ml of filtrate plus 9 ml of Z buffer was used for titers >10 PFU, and negative controls (0 PFU) were done both ways.
[b]An additional three samples turned positive 1.5 h after the end of the designated 30 min incubation period.
[c]An additional three samples turned positive 1.5 h after the end of the designated 30 min incubation period.

At no time throughout the entire study did the liquid method produce a false-positive result, and the incidence of false-negative results only became apparent at extremely low coliphage titers. In order to reduce the rate of false-negative results under low coliphage titers (0–10 PFU), it is advisable that 2 ml of filtrate be added to 8 ml of Z buffer and the incubation time be extended for a peirod not to exceed a total of two hours. Due to the high sensitivity of the assay, all materials used must be cleaned of any residual coliphage particles that could possibly lead to a false positive test. Positive and negative controls should be used to ensure proper functioning of the liquid, colorimetric presence-absence coliphage detection system and method.

The liquid, colorimetric presence-absence detection system and method can be proportioned to accommodate a wide range of water sample volumes by keeping all chemicals in ratio to the 1.25 ml concentrated water sample volume described above. For example, if the final volume of the water sample after concentration is approximately 5 ml, but no greater, inoculate 100 ml LB broth with 500 μl of the 12 h *E. coli* strain C culture, and add 100 μl IPTG. Keep the CPRG and Z buffer volumes, and all incubation times the same. If water concentration is not feasible, unconcentrated water samples can be analyzed using the liquid assay, but multiple replications should be done in order to ensure proper representation of the entire volume of sample collected.

Agar systems are not as convenient as liquid based systems in detecting coliphages in environmental samples. One problem with the use of the plaque count technique for use with environmental samples is the appearance of plaque-like cytotoxic areas in the agar, caused by nonviral toxic materials from the sample. These "false-positive" plaques can distort the results of an agar based system. In addition, some agar systems may not be suitable for detecting low numbers of coliphages. The American Public Health Association (APHA) only recommends their agar-based procedure discussed above when the coliphage number exceeds five plaque forming units (PFU) per 100 ml of sample. Furthermore, there is some difficulty in accurately determining the coliphage density with APHA agar medium where the plaques formed are not permanent and, should overgrowth of the plaques by non-infected bacteria occur, an accurate plaque count cannot be obtained. Moreover, using agar media is cumbersome and time consuming, especially when processing large numbers of water samples.

The liquid, colorimetric, presence-absence coliphage detection system and method does not suffer from any of the limitations of agar based systems and methods. Under certain conditions, it is only important to know whether or not coliphages are present or absent in a water sample. In these instances, the liquid, colorimetric, presence-absence coliphage detection system and method provides a quick and accurate indication of the presence or absence of coliphages. In situations where coliphage quantification is the ultimate goal, it is proposed that the liquid based system and method be used as a complementary test along with an agar based system and method, such as the those described by the inventors or the assay proposed by APHA. Used in this manner, the liquid assay would be a time saving tool especially when evaluating large numbers of water samples because only those samples that tested coliphage positive by the liquid assay would need to be further quantified using an agar medium system and method.

Field experiments have shown that bacteria and extraneous particulate debris which may be found in water samples taken from streams, treatment facilities, wells, etc, need not be removed by filtration prior to using the coliphage detection systems of this invention.

The presence of coliphages in water samples is indicative of viral contamination. The increased sensitivity of the agar-based system and method and the sensitivity/speed of the liquid based system and method will allow routine and accurate viral contamination testing to be performed in order to reduce the potential for human infection by enteric viruses in contaminated water, thereby increasing the overall safety of potable water supplies.

It should be understood that any *E. coli* strain, combination of strains, or mutants of *E. coli* could be used within the practice of this invention. All that is required is that the *E. coli* strain be capable of serving as a host for β-galactosidase production and be susceptible to phage infection and lysis. A particular variation on this invention would be to utilize a strain of *E. coli* which has mutations leading to high levels of constitutive β-galactosidase (e.g., either a lacI$^-$ or lacO$^c$ mutant).

In addition to the colorimetric reagents CPRG and X-gal, the invention could be practiced using different β-galactosidase substrates. For instance, increased sensitivity and speed of detection might be achieved using chemiluminescent substrates (e.g., Lumi-Gal™ which is a phenyl-galactose-substituted dioxetane) or fluorescent substrates (e.g., fluorescein digalactoside or 4-methylumbelliferyl-β,D-galactoside (MUG)) in the liquid or agar media to detect lyric cell infection caused by coliphages.

While the invention has been described in terms of its preferred embodiments, those skilled in the art will recognize that the invention can be practiced with modification within the spirit and scope of the appended claims.

We claim:

1. A method for detecting coliphage in water samples, comprising the steps of:
    combining *E. coli* having intracellular β-galactosidase with a water sample;
    allowing coliphage in said water sample to lyse said *E. coil* to thereby release said β-galactosidase;
    separating *E. coli* from said water sample to produce a bacteria free portion of said water sample;
    adding a substrate which undergoes a detectable change when cleaved by β-galactosidase to said bacteria free portion of said water sample; and
    detecting whether said water sample contains coliphage by said detectable change in said substrate by reaction with said β-galactosidase in said bacteria free portion of said water sample.

2. The method of claim 1 wherein said step of adding a substrate includes the step of selecting a colorimetric reagent as said substrate, and step of detecting is performed by monitoring a change in color of said substrate.

3. The method of claim 1 wherein said step of adding a substrate includes the step of selecting a chemiluminescent compound as said substrate, and said step of detecting is performed by monitoring light emanating from said substrate.

4. The method of claim 1 wherein said step of adding a substrate includes the step of selecting a fluorometric compound as said substrate, and said step of detecting is performed by monitoring fluorescence emanating from said substrate.

5. The method of claim 1 further comprising the step of inducing production of said intracellular β-galactosidase in said *E. coli*.

6. The method of claim 1 wherein said *E. coli* are *E. coli* strain C.

7. A method for quantifying the number of coliphage in water samples, comprising the steps of:
    obtaining a culture of *E. coli* having a known cell density, said *E. coli* having intracellular β-galactosidase;
    obtaining a water sample;
    obtaining a colorimetric substrate which undergoes a color change when cleaved by β-galactosidase;
    combining said water sample, said substrate, and said culture of *E. coli* together in an agar medium;
    incubating said agar medium;
    allowing coliphages in said water sample to lyse said *E. coli*, thereby releasing said β-galactosidase to react with said substrate to produce said color change; and
    detecting said color change in said agar medium.

8. The method of claim 7 wherein said step of obtaining said colorimetric substrate includes the step of selecting a reagent from the group consisting of O-nitrophenyl-β-D-thiogalactoside, 5-bromo-4-chloro-3-indoyl-β-D-galactoside, and chlorophenol red β-D-galactopyranoside.

9. The method of claim 7 wherein said *E. coli* are *E. coli* C.

* * * * *